(12) United States Patent
Schiffman et al.

(10) Patent No.: US 9,707,099 B2
(45) Date of Patent: Jul. 18, 2017

(54) ANTERIOR LUMBAR FUSION METHOD AND DEVICE

(71) Applicant: NuTech Spine, Inc., Birmingham, AL (US)

(72) Inventors: Jeffrey S. Schiffman, Rancho Santa Fe, CA (US); Robert K. Eastlack, San Diego, CA (US); Richard S. Maly, San Diego, CA (US); Howard P. Walthall, Jr., Birmingham, AL (US)

(73) Assignee: NuTech Spine, Inc., Birmingham, AL (US)

(*) Notice: Subject to any disclaimer, the term of this patent is extended or adjusted under 35 U.S.C. 154(b) by 437 days.

(21) Appl. No.: 14/211,837

(22) Filed: Mar. 14, 2014

(65) Prior Publication Data

US 2014/0277502 A1    Sep. 18, 2014

Related U.S. Application Data

(60) Provisional application No. 61/793,616, filed on Mar. 15, 2013.

(51) Int. Cl.
*A61F 2/44* (2006.01)
*A61F 2/46* (2006.01)
*A61F 2/30* (2006.01)

(52) U.S. Cl.
CPC ............ *A61F 2/4611* (2013.01); *A61F 2/447* (2013.01); *A61F 2/4684* (2013.01); *A61F 2002/3055* (2013.01); *A61F 2002/3082* (2013.01); *A61F 2002/30904* (2013.01); *A61F 2002/448* (2013.01); *A61F 2002/4475* (2013.01); *A61F 2002/4627* (2013.01); *A61F 2002/4629* (2013.01)

(58) Field of Classification Search
CPC .......... A61F 2/44; A61F 2/4455; A61F 2/447; A61F 2/4611
USPC ............................................ 623/17.11–17.16
See application file for complete search history.

(56) References Cited

U.S. PATENT DOCUMENTS 4,950,296 A     8/1990   McIntyre
5,484,437 A  *  1/1996   Michelson ......... A61B 17/1671
                                                   128/898

(Continued)

OTHER PUBLICATIONS

Subach, Brian R., et al., Anterior Lumbar Interbody Implants: Importance of the Interdevice Distance. Research Advances in Orthopedics, vol. 2011, Article ID 176497, 5 pages.

(Continued)

*Primary Examiner* — Eduardo C Robert
*Assistant Examiner* — Michelle C Eckman
(74) *Attorney, Agent, or Firm* — C. Brandon Browning; Maynard, Cooper & Gale, PC

(57) ABSTRACT

A method and devices for placing spinal implants including placing the implants completely within a spaced defined between adjacent vertebral bodies where the implants are supported by the cortical bone of the vertebral bodies. An insertion instrument places the implants in pairs with a variable-sized space placed in between. The implants are made of a biocompatible material and are particularly suited for anterior lumbar interbody fusion surgery. The spinal implants used to facilitate spinal fusion, correct deformities, stabilize and strengthen the spine.

27 Claims, 9 Drawing Sheets

(56) References Cited

U.S. PATENT DOCUMENTS

| | | | |
|---|---|---|---|
| 5,593,409 A * | 1/1997 | Michelson | A61B 17/1671 606/247 |
| 5,609,636 A * | 3/1997 | Kohrs | A61F 2/4455 606/247 |
| 5,716,415 A * | 2/1998 | Steffee | A61F 2/447 623/17.16 |
| 5,904,719 A * | 5/1999 | Errico | A61F 2/446 623/17.16 |
| 6,080,155 A | 6/2000 | Michelson | |
| 6,096,038 A | 8/2000 | Michelson | |
| 6,096,081 A | 8/2000 | Grivas et al. | |
| 6,171,339 B1 * | 1/2001 | Houfburg | A61B 17/1757 606/279 |
| 6,210,412 B1 * | 4/2001 | Michelson | A61F 2/30744 606/279 |
| 6,270,498 B1 | 8/2001 | Michelson | |
| 6,290,724 B1 * | 9/2001 | Marino | A61F 2/4455 623/17.11 |
| 6,371,988 B1 | 4/2002 | Pafford et al. | |
| 6,447,544 B1 | 9/2002 | Michelson | |
| 6,485,517 B1 * | 11/2002 | Michelson | A61B 17/7059 623/17.11 |
| 6,508,818 B2 * | 1/2003 | Steiner | A61B 17/7002 606/286 |
| 6,610,089 B1 * | 8/2003 | Liu | A61B 17/025 623/16.11 |
| 6,613,091 B1 * | 9/2003 | Zdeblick | A61B 17/1671 623/17.11 |
| 6,723,096 B1 * | 4/2004 | Dorchak | A61B 17/025 606/279 |
| 6,749,636 B2 | 6/2004 | Michelson | |
| 6,758,849 B1 * | 7/2004 | Michelson | A61F 2/30744 606/247 |
| 6,923,810 B1 * | 8/2005 | Michelson | A61F 2/30771 606/247 |
| 6,926,737 B2 * | 8/2005 | Jackson | A61F 2/446 623/17.11 |
| 6,942,698 B1 * | 9/2005 | Jackson | A61F 2/4455 606/247 |
| 7,022,137 B2 | 4/2006 | Michelson | |
| 7,156,875 B2 * | 1/2007 | Michelson | A61F 2/4455 623/17.11 |
| 7,291,149 B1 * | 11/2007 | Michelson | A61B 17/1757 606/86 A |
| 7,455,692 B2 * | 11/2008 | Michelson | A61F 2/4455 623/17.11 |
| 7,618,423 B1 * | 11/2009 | Valentine et al. | 606/99 |
| 7,655,027 B2 * | 2/2010 | Michelson | A61F 2/44 606/279 |
| 7,867,277 B1 * | 1/2011 | Tohmeh | A61F 2/4455 623/17.11 |
| 8,388,687 B2 * | 3/2013 | Gimbel | A61F 2/4405 606/99 |
| 8,623,088 B1 * | 1/2014 | Tohmeh | A61F 2/4455 623/17.11 |
| 2001/0016741 A1 * | 8/2001 | Burkus | A61B 17/025 606/57 |
| 2001/0032018 A1 * | 10/2001 | Castro | A61F 2/446 623/17.11 |
| 2002/0049499 A1 * | 4/2002 | Walkenhorst | A61F 2/446 623/17.16 |
| 2002/0068936 A1 * | 6/2002 | Burkus | A61B 17/025 606/57 |
| 2002/0111680 A1 * | 8/2002 | Michelson | A61F 2/28 623/17.11 |
| 2002/0138146 A1 * | 9/2002 | Jackson | A61F 2/4455 623/17.15 |
| 2002/0138147 A1 * | 9/2002 | Cohen | A61F 2/4455 623/17.16 |
| 2003/0125739 A1 * | 7/2003 | Bagga et al. | 606/61 |
| 2004/0199168 A1 * | 10/2004 | Bertagnoli | A61B 17/025 606/99 |
| 2004/0249461 A1 * | 12/2004 | Ferree | A61F 2/2846 623/17.11 |
| 2005/0038511 A1 * | 2/2005 | Martz | A61B 17/1606 623/17.11 |
| 2005/0113916 A1 * | 5/2005 | Branch | A61F 2/4611 623/17.11 |
| 2005/0267578 A1 | 12/2005 | Michelson | |
| 2006/0217806 A1 * | 9/2006 | Peterman et al. | 623/17.11 |
| 2010/0217394 A1 | 8/2010 | Michelson | |
| 2011/0301710 A1 * | 12/2011 | Mather et al. | 623/17.16 |
| 2012/0029639 A1 * | 2/2012 | Blackwell | A61F 2/447 623/17.16 |
| 2014/0200668 A1 * | 7/2014 | Kirschman | A61B 17/025 623/17.16 |
| 2014/0277502 A1 * | 9/2014 | Schiffman | A61F 2/4611 623/17.16 |
| 2015/0057755 A1 * | 2/2015 | Suddaby | A61F 2/447 623/17.16 |

OTHER PUBLICATIONS

Taylor, Brett A., et al., The Risk of Foraminal Violation and Nerve Root Impingement After Anterior Placement of Lumbar Interbody Fusion Cages. Spine vol. 26, No. 1, pp. 100-104.

* cited by examiner

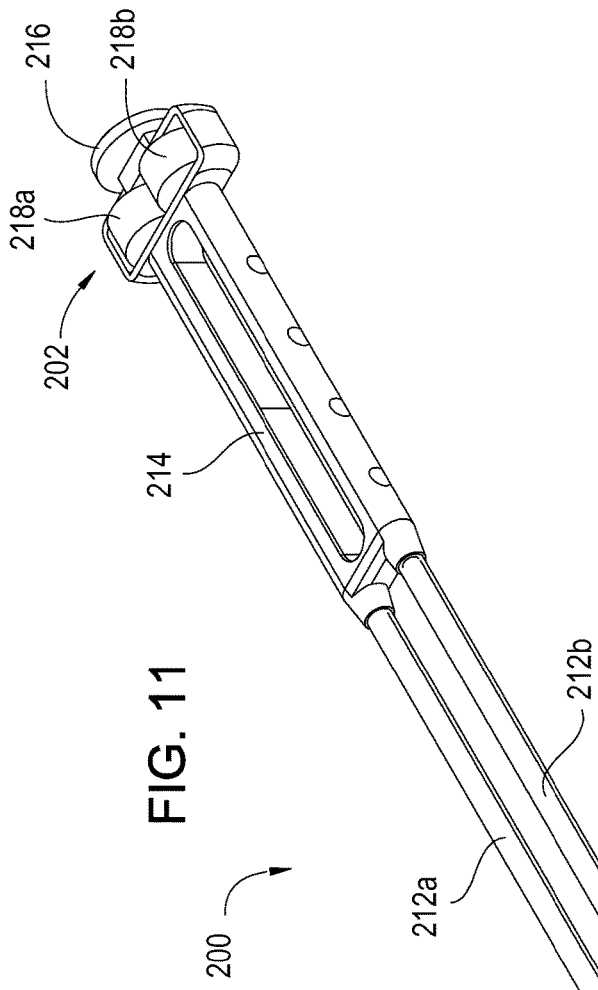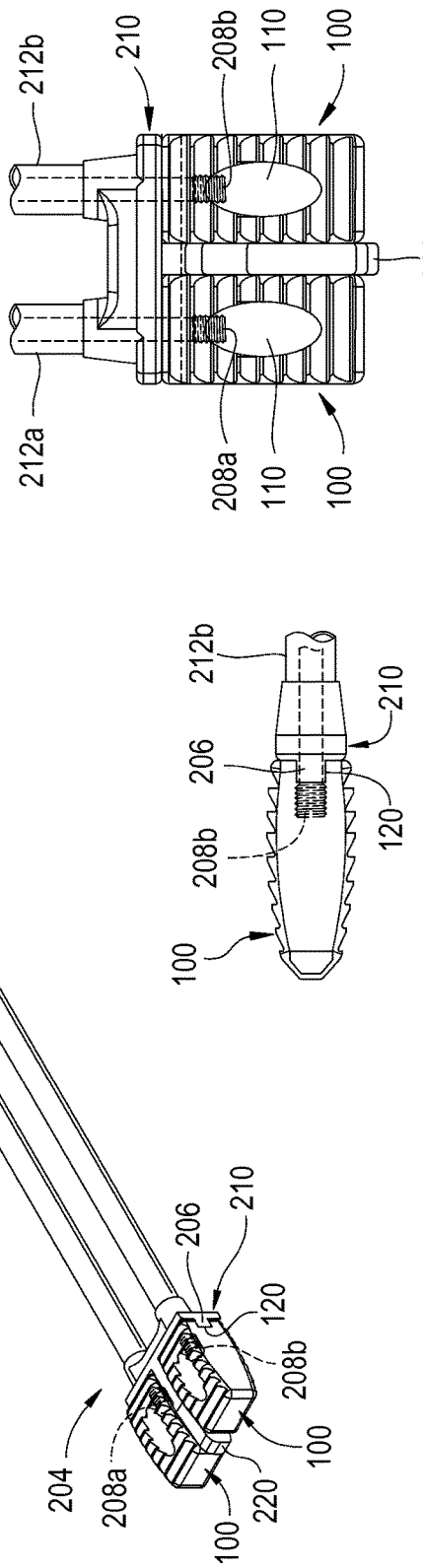
FIG. 11
FIG. 12
FIG. 13

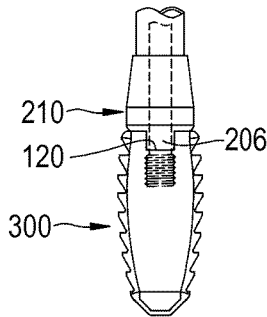 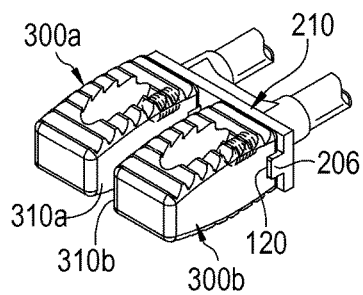 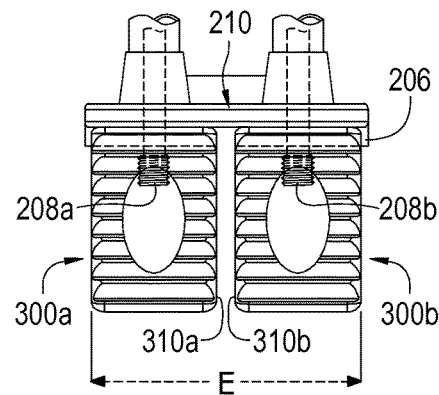
FIG. 14A   FIG. 14B   FIG. 14C
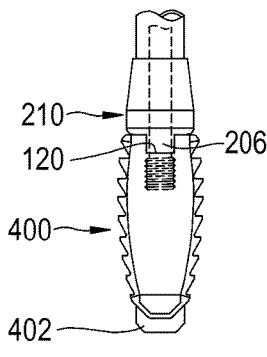 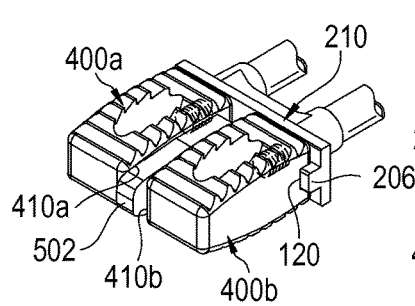 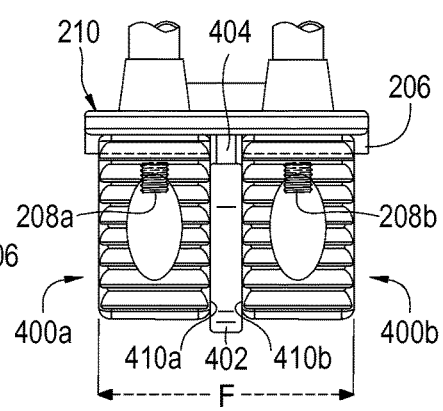
FIG. 15A   FIG. 15B   FIG. 15C
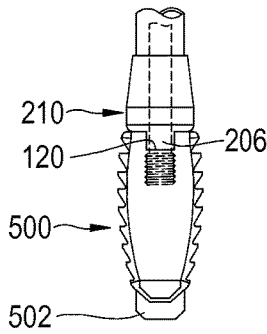 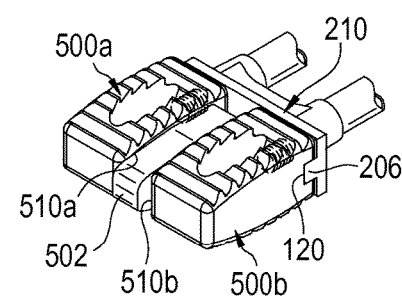 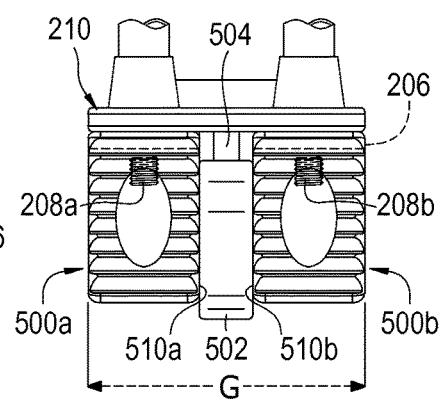
FIG. 16A   FIG. 16B   FIG. 16C

ANTERIOR LUMBAR FUSION METHOD AND DEVICE

RELATED APPLICATIONS

This application claims priority to U.S. Provisional Patent Application No. 61/793,616, filed on Mar. 15, 2013 and titled, "Anterior Lumbar Fusion Method and Device," the entire contents of which are incorporated herein by reference.

FIELD OF THE INVENTION

The present invention relates to methods and devices for placing spinal implants. More particularly, the invention is directed to spinal implants used to facilitate spinal fusion and correct deformities and stabilize and strengthen the spine. The implants are inserted in pairs with a variable-sized space placed in between. The implants are made of a biocompatible material and are particularly suited for anterior lumbar interbody fusion surgery.

BACKGROUND OF THE INVENTION

Anterior lumbar interbody fusion (ALIF) is a surgical procedure used to join two or more vertebrae. Interbody fusion includes removing an intervertebral disc and replacing the disc with an implant. The implant may be naturally occurring, for instance bone tissue, or it may be a non-naturally occurring substance, such as a plastic or plastic derivative. Often, supplementary bone tissue is used in conjunction with non-natural implants to fuse the vertebrae. Spinal fusion procedures are performed to alleviate pain due to abnormal motion of the vertebrae usually caused by degenerative conditions. However, spinal fusion is also the preferred way to treat spinal deformities.

In ALIF, the vertebral disc space is fused by approaching the spine through the abdomen instead of through the lower back. A three-inch to five-inch incision is made on the left side of the abdomen and the abdominal muscles are retracted to the side. The anterior abdominal muscle in the midline runs vertically and therefore does not need to be cut and easily retracts to the side.

Interbody spinal fusion places the implant between the vertebrae in the area usually occupied by the intervertebral disc. In preparation for the spinal fusion, the disc is removed entirely. A device may be placed between the vertebra to maintain spine alignment and disc height. After surgery, fusion occurs between the endplates of the vertebrae. Fusion is augmented by a process called fixation, where metallic screws, rods or plates, or cages are used to stabilize the vertebra and facilitate bone fusion.

Spinal implants generally have a structure which allows for the fusion of adjacent vertebral bodies by promoting growth of bone through the implant. The implant is sized to fit (both in length and width) in the space normally occupied by the vertebral disk. However, the size and shape of the implant is limited by the natural contours of the spine and the vertebral body. Present methods often involve drilling or cutting into the vertebrae in order to secure the implant. These procedures may weaken the vertebral structure and may contribute to failure of the implant. Therefore, one challenge encountered in spinal implant surgical procedures is manufacturing an implant that replicates the general dimensions of the intervertebral disk. An implant that matches the dimensions of the intervertebral disk will more securely reside in the disk space. Elimination, or at least minimization, of movement promotes faster and more efficient fusion with the vertebrae. It may therefore be advantageous to insert multiple implants of a smaller size into the vertebral disk area to insure a better fit. The size of the implants and the spacing of these multiple implants within the disk area will vary depending on the anatomy of the individual patient. What is needed in the art, therefore, is an anterior lumbar interbody fusion method and device which allow for custom spacing of multiple implants.

SUMMARY OF THE INVENTION

In one embodiment, the present invention relates to methods and devices for placing spinal implants. The implants are sized so as to be inserted between vertebral bodies in at least pairs. The interbody implants are placed completely within the space previously occupied by the intervertebral disc and are supported between the cortical bone surfaces of the adjacent vertebrae. The method does not require drilling or boring into the vertebral bone. The height of the implants is larger in the middle than at the ends providing for a convex shape. The convex shape allows the bottom portion of the implant to contact the vertebral body. This maximizes the contact surface area between the implant and the adjacent vertebral bodies and provides improved support to the adjacent vertebrae and thus inhibited movement of the implant after insertion. An insertion instrument places the implant in at least pairs with a variable-sized space placed in between. The spinal implants are used to facilitate spinal fusion, correct deformities, stabilize and strengthen the spine. The implants are made of a biocompatible material and are particularly suited for anterior lumbar interbody fusion surgery.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

FIG. 11 is a perspective view of a spinal implant insertion tool in accordance with an embodiment of the present invention illustrating the tool holding two of the spinal implants of FIG. 4.

FIG. 12 is an elevational view of a lateral side of a spinal implant engagement device of the spinal implant insertion tool of FIG. 11.

FIG. 13 is a top plan view of the view of the spinal implant engagement device of FIG. 12.

FIG. 14a is an elevational view of lateral side of a spinal implant engagement device for use with the spinal implant insertion tool of FIG. 11 with no spacer.

FIG. 14b is a perspective view of the spinal implant engagement device of FIG. 14a.

FIG. 14c is a top plan view of the spinal implant engagement device of FIG. 14a.

FIG. 15a is an elevational view of a lateral side of a spinal implant engagement device for use with the spinal implant insertion tool of FIG. 11 with a first spacer.

FIG. 15b is a perspective view of the spinal implant engagement device of FIG. 15a.

FIG. 15c is a top plan view of the spinal implant engagement device of FIG. 15a.

FIG. 16a is an elevational view of a lateral side of a spinal implant engagement device for use with the spinal implant insertion tool of FIG. 11 with a second spacer.

FIG. 16b is a perspective view of the spinal implant engagement device of FIG. 16a.

FIG. 16c is a top plan view of the spinal implant engagement device of FIG. 16a.

DETAILED DESCRIPTION

Figure 1:
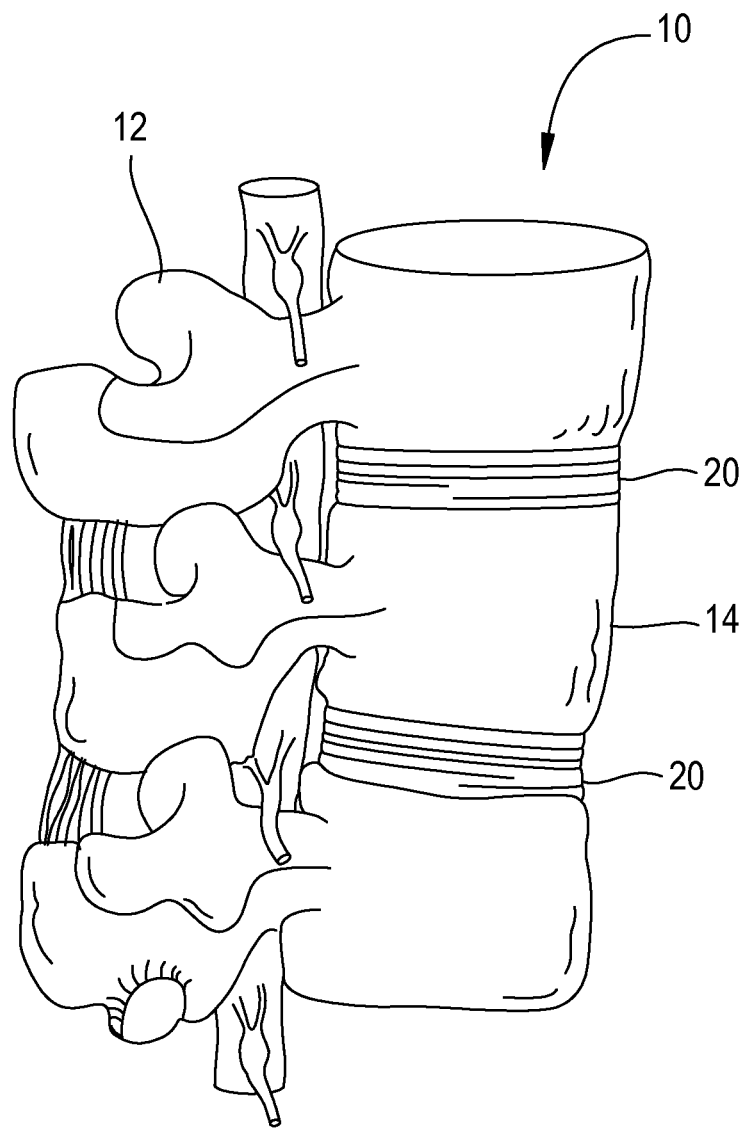
FIG. 1 is a lateral view of a human lumbar spine and spinal cord.

As FIG. 1 shows, the spinal column 10 includes a number of uniquely shaped bones, called the vertebrae 12. The number of vertebrae 12 that make up the spinal column 10 depends upon the species of animal. In a human there are twenty-four vertebrae 12, including seven cervical vertebrae, twelve thoracic vertebrae and five lumbar vertebrae.

Figure 2:
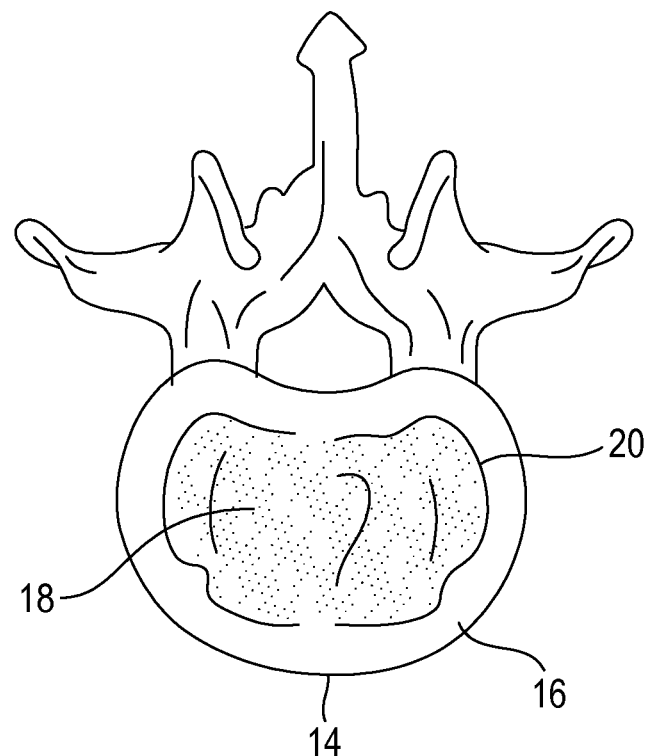
FIG. 2 is top view of a human vertebra.
Figure 3:
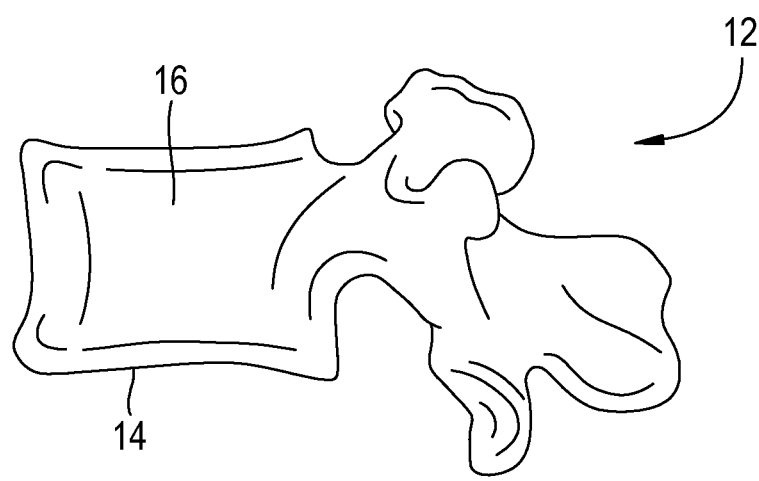
FIG. 3 is a lateral view of a human vertebra.

As FIGS. 1 to 3 show, each vertebra 12 includes a vertebral body 14, which extends on the anterior (i.e., front or chest) side of the vertebra 12. As FIGS. 1 to 3 show, the vertebral body 14 is in the shape of an oval disk. Referring to FIG. 2, the vertebral body 12 includes an exterior formed from compact cortical bone 16. The cortical bone 16 encloses an interior volume of reticulated cancellous, or spongy, bone 18 (also called medullary bone or trabecular bone) and is raised to form a lip that encircles the cancellous bone. A "cushion," called an intervertebral disk 20, is located between vertebral bodies 14.

FIGS. 4 to 10 illustrate an interbody spinal implant 100 in accordance with one embodiment of the present invention. Implant 100 has opposed upper portion 102 and lower portion 104 that make contact with adjacent vertebral bodies 14 when inserted into the disc-space between vertebral bodies 14. In one embodiment, the upper 102 and lower 104 portions have a textured surface for engaging the bone of the vertebral bodies 14 and securing the implant. The embodiment illustrated in FIGS. 4 to 10 includes barb-like projections with evenly spaced raised rings or ratchets 116. The ratchets 116 are angled upward in the direction of the anterior end 30 of implant 100. The ratchets 116 resist forces in the direction of the anterior end 30 of the implant 100 and thus prevent movement of implant 100 out from between adjacent vertebral bodies 14. The textured surface may take other forms, for example grooves or raised lines.

Upper portion 102 and lower portion 104 are spaced apart and connected by two opposing sides 106 and 108. If multiple implants 100 are inserted into the disk space 20, opposing sides 106 and 108 of opposing implants 100 will be adjacent to one other. Opposed upper portion 102 and lower portion 104 may also include at least one hole 110 for the application of bone growth and fusion preparations. In one embodiment, implant 100 is at least partially hollow, again allowing for bone regrowth between adjacent vertebral bodies 14.

Figure 4:
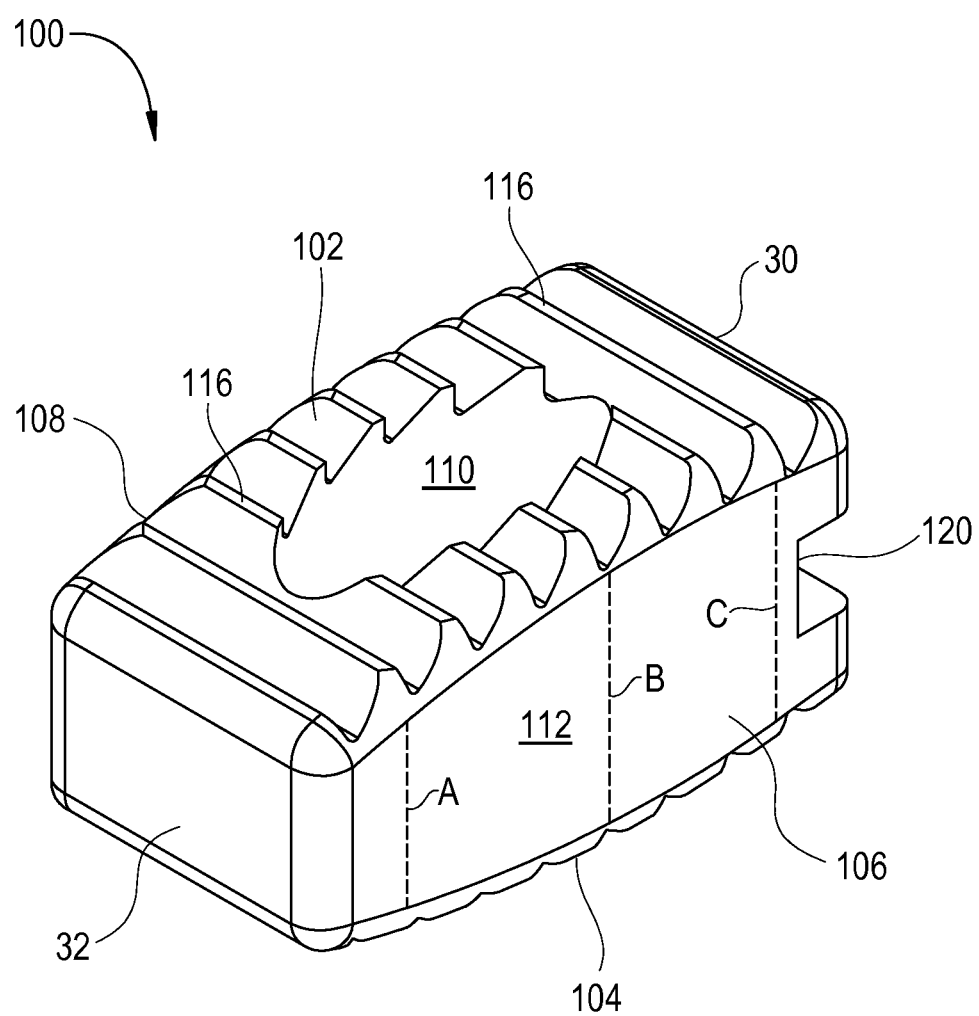
FIG. 4 is a perspective view of a spinal implant in accordance with an embodiment of the present invention.
Figure 5:
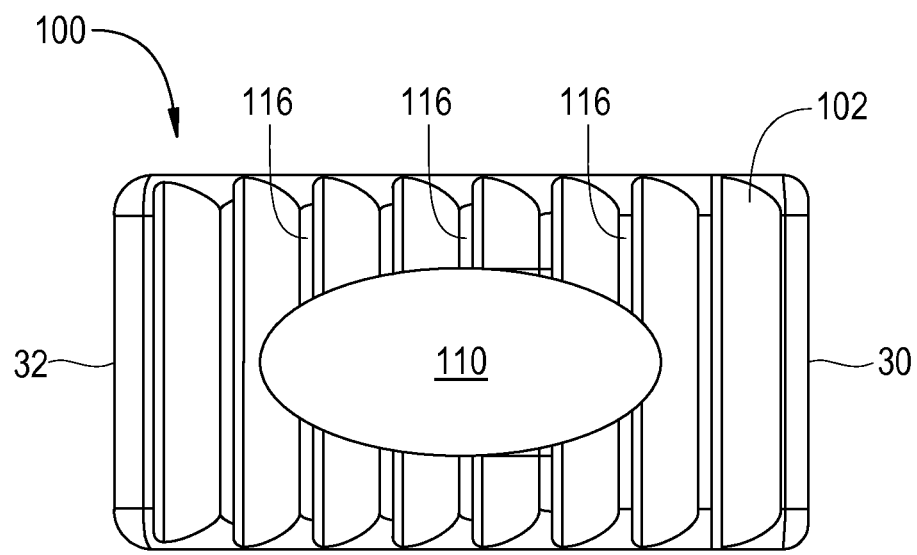
FIG. 5 is a top plan view of the spinal implant of FIG. 4.
Figure 6:
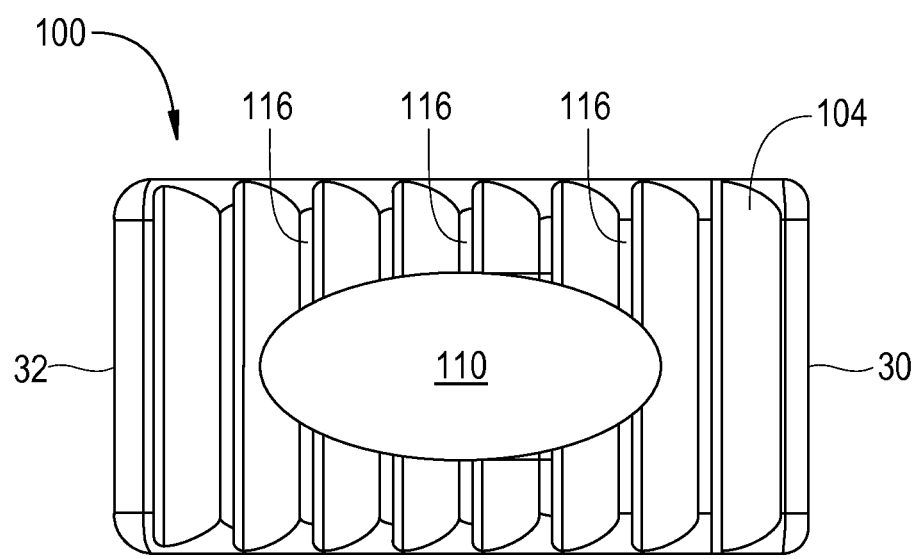
FIG. 6 is a bottom plan view of the spinal implant of FIG. 4.
Figure 7:
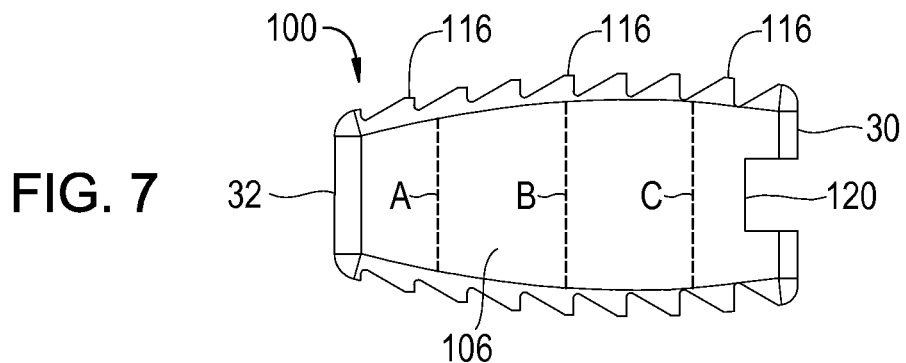
FIG. 7 is an elevational view of a first lateral side of the spinal implant of FIG. 4.
Figure 8:
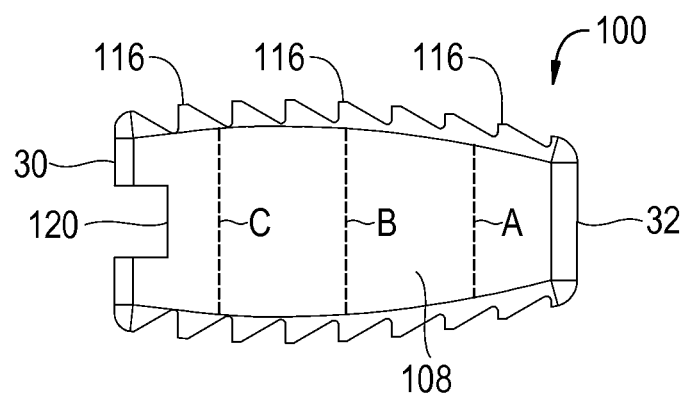
FIG. 8 is an elevational view of a second lateral side of the spinal implant of FIG. 4.
Figure 9:
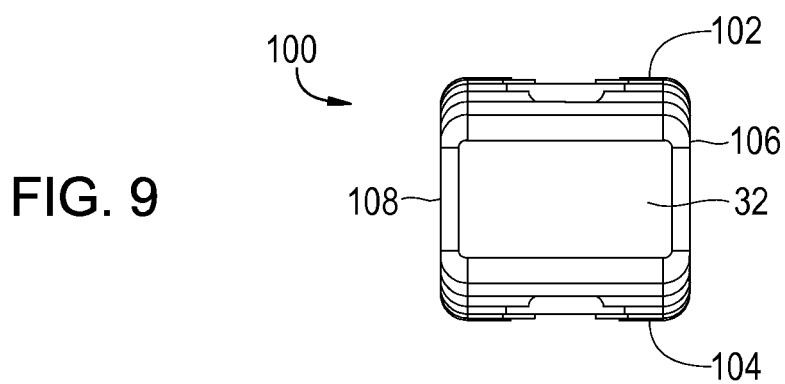
FIG. 9 is an elevational view of a front end of the spinal implant of FIG. 4.
Figure 10:
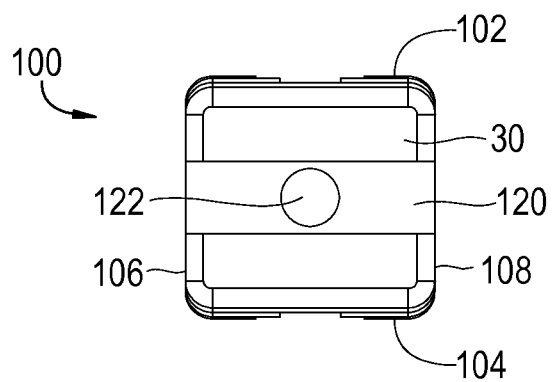
FIG. 10 is an elevational view of a back end of the spinal implant of FIG. 4.

Referring now to FIGS. 4, 7 and 8, implant 100 includes varying heights along its length, as indicated by lines A, B and C. In one embodiment, the length of line B, located at the approximate midpoint of the spacer, is greater than the length of lines A and B. In an additional embodiment, the length of lines A and B may be equal. However, the lengths of lines A and B may not be equal. Implant 100 therefore has a greater height near its center as compared to the anterior 30 and posterior 32 ends, resulting in a convex shape, as will be discussed in more detail below.

Referring now to FIGS. 4, 7, 8 and 10, anterior end 30 of implant 100 includes female groove 120 which runs the length of the anterior end 30. Groove 120 accepts contact slots (not shown) from an insertion device (not shown) which will be discussed in more detail below. The anterior end 30 also includes an opening 122, also used for attachment of the implant 100 to an insertion device (not shown). In one embodiment, opening 122 accepts a screw (not shown) which acts to couple the implant to the insertion device (not shown).

Implants 100 for use in human ALIF may be made of a variety of materials. The material must exhibit strength characteristics to enable formation of a bond between two vertebral segments in the spine. The material must also provide a foundation and environment to allow the body to grow new bone and fuse a section of the spine together. Possible implant materials include autologous bone taken from the patient and transferred to the portion of the spine to be fused, or bone harvested by a tissue bank or a donor. Use of these types of implants is limited because it is often difficult to obtain a bone section large enough and shaped correctly in order to provide the needed vertebral support. There are a variety of bone graft substitutes that are available for use in spine fusion surgery. In general, these types of bone graft are a synthetic or a manipulated type of a naturally-occurring product. Exemplary graft substitutes include demineralized bone matrix (DBM), synthetic bone graft extenders, bone morphogenetic proteins (BMP) and demineralized bone matrix (DBM). Other synthetic materials are also available. One exemplary non-naturally occurring material is polyether ether ketone (PEEK), a colorless organic polymer thermoplastic. PEEK is a semicrystalline thermoplastic with excellent mechanical and chemical resistance properties. Because of its robustness, PEEK is one of the few advanced biomaterials used in medical implants.

In an additional embodiment of the invention, implant 100 is adapted to detachably engage an insertion tool for insertion of the implant 100 into a region of the body. In one embodiment, the anterior end is shaped to engage with an insertion tool. FIG. 11 shows one embodiment of a tool 200 for performing ALIF, having a proximal and distal end, 202 and 204, respectively. The tool 200 includes two hollow tube-like structures 212a and 212b which extend in parallel from the distal end 202 to the proximal end 204. Hollow tubes 212a and 212b terminate at the distal end 204 with an engagement device 210 for securing and placing the spinal implants 100 between the intervertebral bodies 14. Referring now to FIGS. 12 and 13, engagement device 210 includes a raised male slot 206 which connects with female groove 120

(FIGS. 7, 8 and 10) located on implant 100, for instance with a snapping or sliding motion. Engagement of slot 210 within groove 120 secures the implant 100 to the tool 200 for insertion of the implant(s) into the vertebral body 14.

In the embodiment illustrated in FIGS. 11 to 13, hollow tubes 212a and 212b each contain a screw-like device 208a and 208b within their interior. The screws 208a and 208b extend through the entirety of hollow tubes 212a and 212b and protrude from the distal end 204 into the engagement device 210 (FIGS. 12 and 13). The protruding ends of screws 208a and 208b serve to secure the implant 100 to the tool 200 during insertion of the implant(s) into the vertebral body 14. Referring again to FIG. 11, tool 200 further includes handle 214 so that the user may manipulate the device. Knob 216 is placed at the proximal end 202 of the tool. Rotational movement of knob 216 causes a concurrent rotational movement of disks 218a and 218b. Rotation of disks 218a and 218b initiates rotation of screws 208a and 208b into or out of opening 122. As a result, rotation of knob 216 in a first direction acts to secure the implant 100 to the insertion tool 200 (by rotating and inserting screws 208a and 208b into the opening 122) while rotation of knob 216 in the opposite direction acts to release the implant 100 from the vertebral body 14 (by rotation and withdrawing screws 208a and 208b from opening 122).

In one embodiment of the invention, tool 200 secures at least two implants 100 for insertion into the vertebral body 14. The at least two implants 100 are secured to the tool 200 in such a manner that one opposing side 106 of a first implant is adjacent to one opposing side 108 of a second implant. The present invention is not limited to a tool 200 including two implants as presently described and thus contemplates other numbers of implants 100. FIGS. 14 to 16 illustrate the placement of two implants 100 within the engagement device 210. FIG. 14a illustrates an implant 300 secured to the engagement device 210 via connection of a raised male slot 206 to the female groove 120, and via insertion of screws 208a and 208b into opening 122. Engagement of slot 210 within groove 120 detachably secures the implant 100 to the tool 200 during insertion of the implant(s) into the vertebral body 14. FIG. 14b shows a set of implants 300a and 300b secured to the engagement device 210. The two implants 300a and 300b are separated, or spaced, at a distance E (FIG. 14c). Opposing side 310a of the first implant 300a is adjacent to the opposing wall 310b of implant 300b. Turning now to FIGS. 15a-c, implants 400a and 400b are detachably secured to engagement device 210 via connection of a raised male slot 206 to the female groove 120, and via insertion of screws 208a and 208b into opening 122. The two implants 400a and 400b are separated, or spaced, at a distance F (FIG. 15c). The distance F is maintained by insertion of spacer 402 into the engagement device 210. Spacer 402 includes a protruding peg 404 which is detachably mated with a matching hole (not shown) in the center of the engagement device 210. In this embodiment, the distance F is greater than the distance E (FIG. 14c), resulting in a greater spacing between implants 400a and 440b (as compared to spacers 300a and 300b as illustrated in FIG. 14c). Opposing side 410a of the first implant 400a is adjacent to the opposing wall 410b of implant 400b. Similarly, as illustrated in FIGS. 16a-c, implants 500a and 500b are detachably secured to engagement device 210 via connection of a raised male slot 206 to the female groove 120, and via insertion of screws 208a and 208b into opening 122. The two implants 500a and 500b are separated, or spaced, at a distance G (FIG. 15c). The distance G is maintained by the detachable insertion of spacer 502 into the engagement device 210. Spacer 502 includes a protruding peg 504 which mated with a matching hole (not shown) in the center of the engagement device 210. Opposing side 510a of the first implant 500a is adjacent to the opposing wall 510b of implant 500b. In this embodiment, the distance G is greater than the distances E (FIG. 14c) and F (FIG. 15c), resulting in a greater spacing between implants 400a and 440b (as compared to spacers illustrated in FIGS. 14c and 15c).

It can be appreciated by these embodiments that the distance between two implants may be adjusted by inserting the desired sized spacer between the implants and securing the spacer to the engagement device, as herein described. The size of the spacing (and thus the spacer) will vary depending on multiple factors, for instance the size and age of the patient, the health condition currently under treatment and the dimensions of the patient anatomy, as is known to one of skill in the art. The present invention is not limited to use of identically sized implants 100 and instead contemplates insertion of differently sized implants 100 into the vertebral body 14 utilizing the presently described insertion tool.

Figure 17:
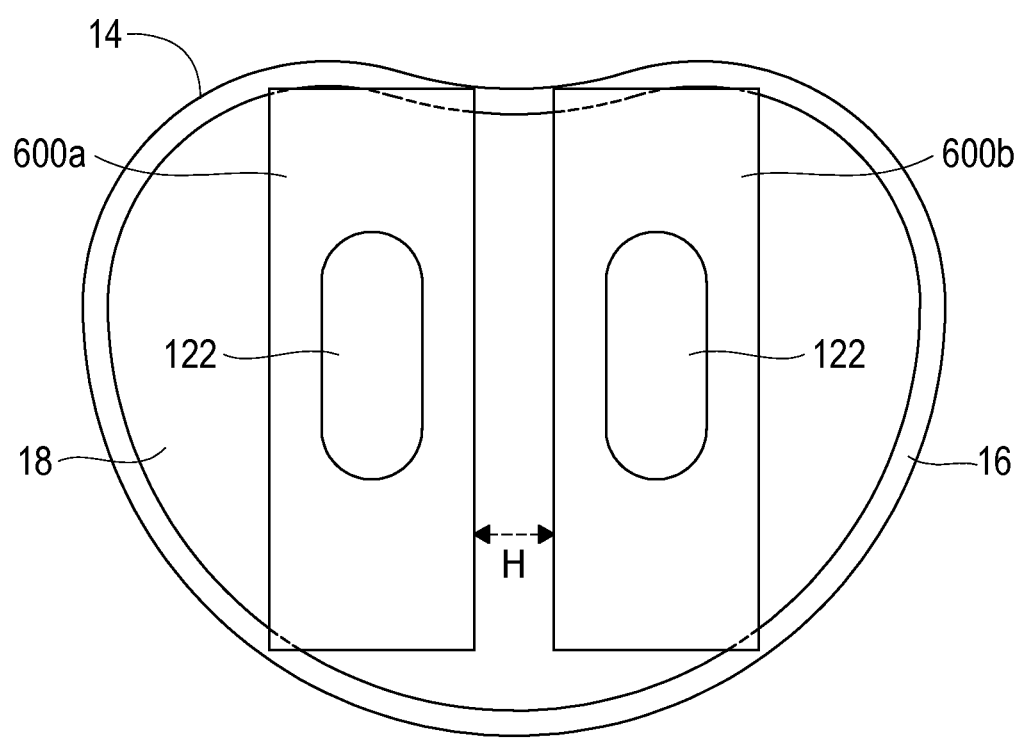
FIG. 17 is a top plan view of a lumbar vertebral body with a first pair of spinal implants in accordance with an embodiment of the invention.

FIG. 17 shows a top plan view of the endplate region of a vertebral body 14 with the outline of the presently disclosed spinal implants 600a and 600b inserted on each side of the vertebral body 14. Here, the implants 600a and 600b are placed so that the bottom side 104 rests on the cortical bone 16, located on the periphery of the vertebral body 14. The cortical bone 16 is the strongest portion of vertebral body 14 and is therefore the most appropriate weight bearing structure. Placement of the implants 600a and 600b on the cortical bone 16 provides support and prevents the necessity of drilling into any of the bones of the vertebral body, thus weakening of the vertebra 12 in general. The two implants 600a and 600b are spaced at an appropriate distance H as determined by a health care professional based upon the physical dimensions of the vertebral body.

Figure 18:
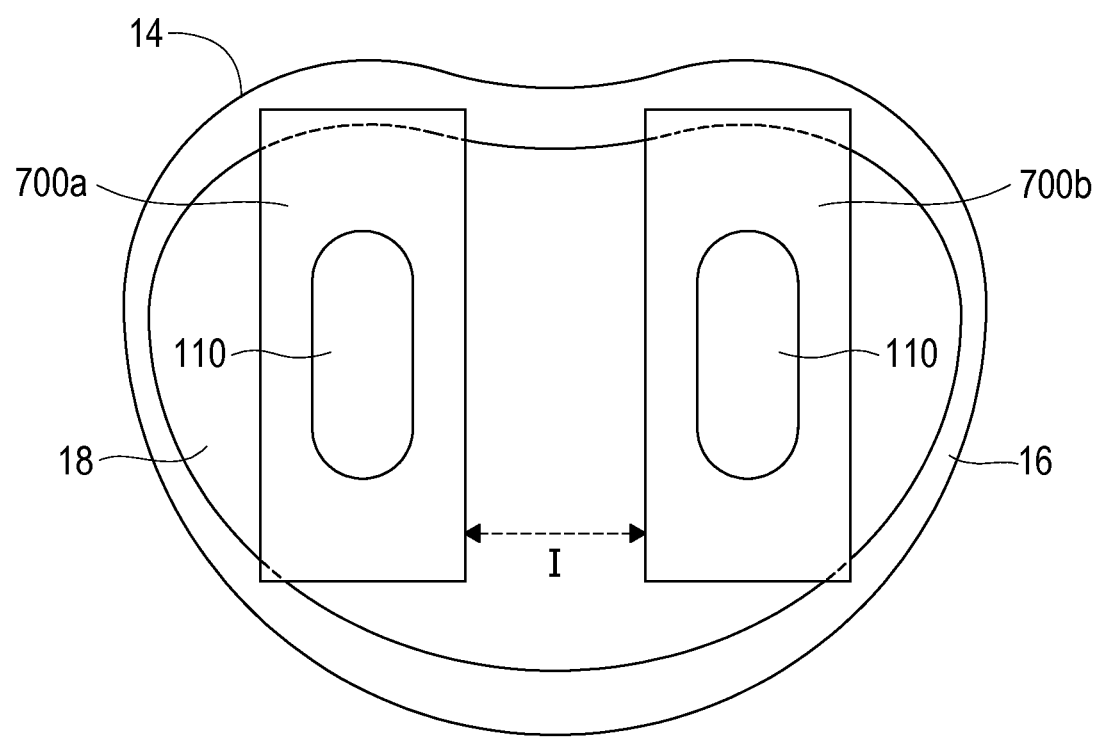
FIG. 18 is a top plan view of a lumbar vertebral body with a second pair of spinal implants in accordance with an embodiment of the invention.

FIG. 18 illustrates a top plan view of the endplate region of a vertebral body 14 similar to that shown in FIG. 17. The outline of the presently disclosed implants 700a and 700b are illustrated as inserted on each side of the vertebral body 14. Implants 700a and 700b are placed so that the bottom side 104 rests in the cortical bone 16, located on the periphery of the vertebral body 14. The two implants 700a and 700b are spaced at an appropriate distance I as determined by a health care professional based upon the physical dimensions of the vertebral body. Here, the physician has determined that a larger spacing H is appropriate to separate implants 700a and 700b. As with the previously described FIG. 17, implants 700a and 700b sit over the cortical bone 16, located on the periphery of the vertebral body 14. Placement in this manner provides the necessary strength and structure needed to support implants 700a and 700b within vertebral body 14.

The overall physical dimensions of the vertebral body 14 limits the size of the implant 100 which may be inserted. Insertion of multiple smaller implants allows for a better fit within the vertebral body 14. Insertion of multiple smaller implants 100 allows for a more precise and more secure fit in the vertebral body 14. The multiple implants 100 provide greater overlap of the cortical bone 16, thus offering greater support and stability.

The present invention is also related to a method of inserting a plurality of spinal inserts between vertebral bodies of a patient. In general, a patient in need of spinal fusion surgery is placed on the operating table in a supine position, i.e., lying down with the face up. The spine may be extended slightly at the surgeon's discretion. A three-inch to five-inch transverse or oblique incision is made just to the left of the umbilicus (belly button). The abdominal muscles are gently spread apart, but are not cut. The peritoneal sac is retracted to the side, as are the large blood vessels. Special retractors are used to allow the surgeon to visualize the anterior aspect of the intervertebral discs. After the retractor is in place, an x-ray is used to confirm that the appropriate spinal level(s) is identified.

The intervertebral disc 20 is then removed using special biting and grasping instruments. Because of the concave shape of the presently described implants 100, removal of bone in the vertebral body 14 is unnecessary. Excessive scraping of the bone may weaken the endplate (not shown in the figures). Special distractor instruments are used to restore the normal height of the disc, as well as to determine the appropriate size of implant to be placed. The physician then inserts a series of differently sized metal or plastic trial plates (not shown) between the adjacent vertebral bodies 14, beginning with a smaller size (length and width) and incrementally increasing the size until a tight fit is obtained. The trial plates act as guides to assist the surgeon in determining the proper size of the spinal implants necessary for insertion into the disc space between the vertebral bodies. Using the trial plates, the surgeon may also determine the optimal spacing between the multiple implants 100 needed to ensure that the implants rest on and are supported by the hard cortical bone 16. This may be done by inserting trial spacers (not shown) between the trial plates in order to obtain the proper spacing. It is important to use the tallest possible implant 100 to provide maximize stability to the vertebral body 14. It is possible that two differently sized implants are utilized concurrently to properly support the adjacent vertebra 12 due to the non-symmetrical nature of the vertebral body 14. Exemplary trial plates are shown and described in U.S. Pat. No. 8,454,699.

Once the properly sized trial plates and trial spacers have been determined, the physician removes the trial plates and spacers and obtains implants 100 and spacers 220 (FIG. 13) with sizes corresponding to these trial plates and spacers. With the screws 208 in the retracted position, a first male slot 206 of an implant tool 200 is mated with the female groove 120 of a first appropriately sized implant 100. The appropriately sized spacer is then inserted into the engagement device 210 by inserting the protruding peg (not shown) into a matching hole (not shown). Next, a second male slot 206 of an implant tool 200 is mated with the female groove 120 of a second appropriately sized implant 100. The second implant is located adjacent to the first implant. The two implants are separated by spacer 220. The physician then grasps tool 100 by the handle 215 and rotates knob 216. The rotational force of knob 216 turns rotating disks 218 in a direction causing screws 208 to rotate and engage the opening 122, thus securing the implants 100 to the engagement device 210.

The surgeon then inserts the secured implants 100 into the previously evacuated disc space between the adjacent vertebral bodies 14. The posterior ends 32 of the secured implants are first inserted in a linear direction into the space, moving in a direction from the anterior (front) portion of the body to the posterior (back) portion of the body. The implants 100 should be properly size and spaced as their dimensions were determined using the trial plates and the trial spacers as previously detailed. The concave shape of implants 100 (see FIGS. 4, 7 and 8) allows the bottom opposing side 104 to make contact with the surface of the lower vertebral body 14 and the top opposing side 102 to make contact with the adjacent vertebral body 14 and prevents their movement beyond the vertebral body 14. In this embodiment of the invention, when implants 100 are inserted between two adjacent vertebral bodies 14, implants 100 are completely contained there between. No portion of implants 100 protrude from the spine, minimizing injury to the spinal cord or any major blood vessels.

The surgeon then verifies that the implants 100 are (1) securely inserted between the vertebral body 14, (2) fully resting on the cortical bone 16 and (3) completely contained between the vertebral bodies 14. This may be accomplished in a number of ways as are known to one in the art, for instance by X-ray analysis or fluoroscopy. The surgeon then grasps tool 100 by the handle 215 and rotates knob 216 in the direction opposite of that used to secure the implants 100 as described above. The rotational force of knob 216 turns rotating disks 218 in a direction causing screws 208 to rotate and disengage from opening 122. The insertion tool 200 is then gently moved to dislodge the male slot 206 of the implant tool 200 from the female groove 120 of implants 100, thus releasing the implants 100 from the engagement device 210. The insertion tool 200 is then removed from between the vertebral bodies 14 while the implants remain. The ratchets 116 located on the top side 102 and bottom side 104 of implant 100 resist forces in the direction of the anterior end 30 of the implant 100 and thus prevent movement of implant 100 out from between the vertebral bodies 14. Spacer 220 remains engaged with the engagement device 210 and is therefore removed from between the vertebral bodies upon retraction of the insertion tool 200. The physician may again verify that the implants are properly inserted within the vertebral body space.

In an additional embodiment, a bone graft substance, for instance implant materials as described previously, is then injected within the hollow interior of inserts 100. The substance may also include ground bone mixed with other growth promoting materials, such as bone morphogenic proteins. In one embodiment, the bone graft substance is injected through opening 100, to promote bone regeneration around the implants and fusion of the affected vertebrae. The substance may alternatively be placed into the hollow spaces of the implants prior to implantation. Fusion may be augmented by the insertion of metallic screws, rods or plates, or cages on the periphery of the vertebrae.

Now, therefore, the following is claimed:

1. A method of inserting spinal implants between adjacent vertebral bodies comprising:
   detachably engaging an anterior end of a first spinal implant and an anterior end of a second spinal implant to a distal end of a spinal implant insertion tool, wherein the first spinal implant is detachably engaged with threads of a first screw member of the spinal implant insertion tool and the second spinal implant is detachably engaged with threads of a second screw member of the spinal implant insertion tool,
   using the spinal implant insertion tool to insert the first spinal implant and the second spinal implant simultaneously between a pair of adjacent vertebral bodies, and
   detaching the spinal insertion tool from the first spinal implant and the second spinal implant thereby depositing the first implant and the second implant between the pair of adjacent vertebral bodies,
   wherein the first spinal implant and the second spinal implant are detached from the spinal insertion tool by manipulating a rotatable member operatively coupled to the first screw member and the second screw member.

2. The method according to claim 1 further comprising obtaining at least one measurement of a disc-space defined between the first spinal implant and the second spinal implant.

3. The method according to claim 2 further comprising selecting the first spinal implant and the second spinal implant from a plurality of spinal implants having sizes differing from sizes of the first spinal implant and the second spinal implant based upon the at least one measurement.

4. The method according to claim 2 further comprising spacing the first spinal implant a predetermined distance from the second spinal implant within the disc-space based upon the at least one measurement.

5. The method according to claim 2 further comprising using at least one trial plate to obtain the at least one measurement.

6. The method according to claim 1 further comprising supporting a spacer at the distal end of the spinal insertion tool, the spacer being arranged between the first spinal implant and the second spinal implant.

7. The method according to claim 6 wherein the spacer is selected from a plurality of spacers having widths differing from a width of the spacer based upon a dimension of a disc-space defined between the pair of adjacent vertebral bodies.

8. The method according to claim 1 further comprising arranging the first spinal implant between the pair of adjacent vertebral bodies with no edge of the first spinal implant extending outside of a cortical bone lip of at least one vertebral body of the pair of vertebral bodies.

9. The method according to claim 8 further comprising arranging the second spinal implant between the pair of adjacent vertebral bodies with no edge of the second spinal implant extending outside of the cortical bone lip of the at least one vertebral body.

10. The method according to claim 1 wherein no edge of the first spinal implant and no edge of the second spinal implant extends outside of a cortical bone lip of either vertebral body of the pair of vertebral bodies.

11. The method according to claim 1 wherein the first spinal implant and the second spinal implant are supported between a cortical bone lip of a first vertebral body and a cortical bone lip of a second vertebral body.

12. The method according to claim 1 wherein no bone material is removed from the pair of adjacent vertebral bodies.

13. The method according to claim 1 further comprising injecting a bone graft material into a hole in the first spinal implant.

14. The method according to claim 1 further comprising engaging anti-migration ridges on a surface of the first spinal implant with the pair of adjacent vertebral bodies.

15. The method according to claim 1 further comprising arranging a convex upper surface of the first spinal implant to face a lower cancellous bone surface of a first vertebral body of the pair of adjacent vertebral bodies and a convex lower surface of the first spinal implant to face an upper cancellous bone surface of a second vertebral body of the pair of adjacent vertebral bodies.

16. The method according to claim 1 further comprising detaching the spinal insertion tool from the first spinal implant and the second spinal implant simultaneously by rotating the rotatable member and thereby simultaneously rotating the first screw member and the second screw member.

17. The method according to claim 1 comprising rotating the first screw member within a first tube member and the second screw member within a second tube member that is arranged parallel to the first tube member.

18. The method of claim 1 wherein the first spinal implant and the second spinal implant are interbody fusion implants.

19. The method of claim 1 comprising fusing the adjacent vertebral bodies together with the first spinal implant and the second spinal implant being deposited therebetween.

20. A method of inserting spinal implants between adjacent vertebral bodies comprising:
providing a first spinal implant having an upper ridged convex surface, a lower ridged convex surface and opposing lateral sides,
providing a second spinal implant,
detachably engaging the first spinal implant and the second spinal implant to a distal end of a spinal implant insertion tool, wherein the spinal implant insertion tool includes a first screw member to which the first spinal implant is attached, the first screw member being arranged parallel to a second screw member to which the second spinal implant is attached,
coupling a spacer member to the distal end, the spacer member being arranged between the first spinal implant and the second spinal implant,
inserting the first spinal implant and the second spinal implant simultaneously between the adjacent vertebral bodies, and
detaching the spinal insertion tool from the first spinal implant and the second spinal implant thereby depositing the first implant and the second implant between the adjacent vertebral bodies.

21. The method according to claim 20 wherein the first spinal implant is arranged so that no corner of the first spinal implant extends outside of a cortical bone lip of each vertebral body of the adjacent vertebral bodies.

22. The method according to claim 20 further comprising selecting the first spinal implant from a plurality of spinal implants having sizes differing from the first spinal implant based upon a dimension of a disc-space defined between the adjacent vertebral bodies.

23. The method according to claim 20 wherein the spacer is selected from a plurality of spacers having widths differing from a width of the spacer based upon a dimension of a disc-space defined between the adjacent vertebral bodies.

24. The method according to claim 20 further comprising arranging the upper ridged convex surface of the first spinal implant to face a lower cancellous bone surface of a first vertebral body of the adjacent vertebral bodies and the upper ridged convex surface of the first spinal implant to face an upper cancellous bone surface of a second vertebral body of the adjacent vertebral bodies.

25. The method of claim 20 wherein the first spinal implant and the second spinal implant are interbody fusion implants.

26. The method of claim 20 comprising fusing the adjacent vertebral bodies together with the first spinal implant and the second spinal implant being deposited therebetween.

27. The method of claim 20 comprising detaching the spinal implant insertion tool from the first spinal implant and the second spinal implant by rotating a knob that is operatively coupled to the first screw member and the second screw member and thereby simultaneously rotating the first screw member and the second screw member.

* * * * *